(12) United States Patent
Friel (10) Patent No.: US 10,543,975 B2
(45) Date of Patent: Jan. 28, 2020

(54) CANISTER AND VALVE (71) Applicant: AER BEATHA LIMITED, London, Greater London (GB)

(72) Inventor: Michael Friel, London (GB)

(73) Assignee: AER BEATHA LIMITED, London (GB)

(*) Notice: Subject to any disclaimer, the term of this patent is extended or adjusted under 35 U.S.C. 154(b) by 0 days.

(21) Appl. No.: 15/774,630

(22) PCT Filed: Nov. 3, 2016

(86) PCT No.: PCT/GB2016/053406
§ 371 (c)(1),
(2) Date: May 9, 2018

(87) PCT Pub. No.: WO2017/081443
PCT Pub. Date: May 18, 2017

(65) Prior Publication Data
US 2018/0327176 A1  Nov. 15, 2018

(30) Foreign Application Priority Data

Nov. 9, 2015 (GB) .................................... 1519705.6
Apr. 1, 2016 (GB) .................................... 1605547.7

(51) Int. Cl.
*B65D 83/54* (2006.01)
*B65D 83/66* (2006.01)
*A61M 15/00* (2006.01)

(52) U.S. Cl.
CPC ........... *B65D 83/54* (2013.01); *B65D 83/663* (2013.01); *A61M 15/009* (2013.01)

(58) Field of Classification Search
CPC ...... B65D 83/663; B65D 83/54; B65D 83/52; B65D 83/14; B65D 83/60; B65D 83/64;
(Continued)

(56) References Cited

U.S. PATENT DOCUMENTS 3,258,163 A * 6/1966 Brush .................. B65D 83/663
222/61
3,851,799 A   12/1974 Paoletti
(Continued)

FOREIGN PATENT DOCUMENTS

BE      1004019 A3    9/1992
EP    1 475 316 A1   11/2004
(Continued)

OTHER PUBLICATIONS

May 30, 2017 Written Opinion issued in International Patent Application No. PCT/GB2016/053406.
(Continued)

*Primary Examiner* — Lien M Ngo
(74) *Attorney, Agent, or Firm* — Oliff PLC (57) ABSTRACT

A canister for a metered dose inhaler has high and low pressure chambers for a propellant and for an inhalable drug and vaporised propellant. The low pressure chamber has an opening for a metering valve. A pressure regulating valve is between the high and low pressure chambers and provides a flow path from them. A metering valve dispenses a metered dose. The valve includes a metering valve body having a propellant metering chamber with a propellant inlet and a product metering chamber with a product inlet, and a metering valve stem with a dispensing nozzle, a propellant inlet plug and a product inlet plug. The metering valve stem moves to a dispensing position. In the dispensing position, the propellant and product metering chambers are in fluid communication with atmosphere via the dispensing nozzle of the metering valve stem such that a metered dose of product and propellant can be dispensed.

10 Claims, 6 Drawing Sheets

(58) Field of Classification Search
CPC ............ A61M 15/009; A61M 15/0065; A61M 15/0028
USPC ....... 222/402.1, 399, 402.16, 402.18, 402.19
See application file for complete search history.

(56) References Cited

U.S. PATENT DOCUMENTS

| | | | | |
|---|---|---|---|---|
| 4,456,155 | A | * | 6/1984 | Miyata ................ B67D 1/0412 222/396 |
| 5,080,266 | A | | 1/1992 | O'Neill |
| 5,507,420 | A | * | 4/1996 | O'Neill ................ B65D 83/60 141/20 |
| 5,730,326 | A | | 3/1998 | Kaeser |
| 6,305,582 | B1 | * | 10/2001 | Tsutsui .................. B65D 83/48 222/402.24 |
| 6,499,632 | B2 | * | 12/2002 | van't Hoff ............. B65D 83/64 222/389 |
| 2001/0027981 | A1 | | 10/2001 | Yquel |
| 2004/0139965 | A1 | * | 7/2004 | Greenleaf ............. A61M 15/009 128/200.23 |
| 2006/0054237 | A1 | * | 3/2006 | Vanblaere ............. B65D 83/663 141/18 |
| 2008/0308581 | A1 | | 12/2008 | Van't Hoff |
| 2012/0055467 | A1 | | 3/2012 | Brambilla et al. |
| 2013/0019863 | A1 | * | 1/2013 | Stevenson ........... A61M 15/009 128/200.23 |

FOREIGN PATENT DOCUMENTS

| | | |
|---|---|---|
| FR | 2785594 A1 | 5/2000 |
| FR | 2804666 A1 | 8/2001 |
| NL | 7810474 A | 4/1980 |
| WO | WO 88/04638 A1 * | 6/1988 |
| WO | 90/15377 A1 | 12/1990 |
| WO | 95/15895 A1 | 6/1995 |
| WO | 97/36801 A2 | 10/1997 |
| WO | 2004/041340 A2 | 5/2004 |
| WO | 2015/008250 A2 | 1/2015 |

OTHER PUBLICATIONS

May 30, 2017 International Search Report issued in International Patent Application No. PCT/GB2016/053406.
Sep. 9, 2016 Search Report issued in Great Britain Patent Application No. 1605547.7.
Jan. 29, 2016 Search Report issued in Great Britain Patent Application No. 1519705.6.

* cited by examiner

CANISTER AND VALVE

FIELD OF THE INVENTION

The present invention relates to a canister for use in a metered dose inhaler (MDI). In particular, this invention relates to a canister which allows use of a non-conventional propellant for dispensing a dose of medicament from an MDI. In addition, the present invention relates to a metering valve which can be fitted to the canister for use in an MDI.

BACKGROUND OF THE INVENTION

Metered dose inhalers (MDIs) are used to deliver a metered amount of an aerosolised drug directly to the patient's lung by inhalation. They are typically used to deliver drugs comprising bronchodilators (e.g. salbutamol) or corticosteroids (e.g. beclomethasone) for the treatment and control of asthma and Chronic Obstructive Pulmonary Disease (COPD).

The drugs are contained in an aluminium canister which is fitted at its open end with a metering valve. The stem of the metering valve is housed in a nozzle block within an actuator body, the actuator body having a mouth piece portion through which a patient can inhale. The valve is operated to release the metered dose of drug towards the mouth piece by depression of the canister within the actuator body.

In order to propel the drug from the canister in the form of an aerosol, a liquid propellant is contained within the canister along with the drug. The drug is then available for inhalation in the form of a fine mist with the drug dispersed in the high vapour pressure propellant.

A propellant must meet certain criteria. It must be a chemically stable liquefied gas having low toxicity and low flammability. It must be acceptable to patients in terms of taste and smell and it must have appropriate solvency characteristics to allow for drug formulation.

The drug/propellant formulation may either be a suspension formulation with the micro-particulate drug suspended within the propellant or a solution formulation with the drug dissolved in the propellant or in a combination of the propellant and a co-solvent such as ethanol.

Another important consideration in the choosing a propellant is that the vapour pressure must remain constant in order to ensure consistent dosing of the drug.

The earliest MDIs used chlorofluorocarbon (CFC) propellants which have since been phased out and replaced with hydrofluorocarbons (HFCs) due to the undesirable impact on the environment associated with CFC use. Both CFCs and HFCs form a two-phase (liquid and saturated vapour) system within the canister and a dynamic equilibrium exists between the two phases giving a constant vapour pressure irrespective of whether the canister is full or nearly empty. Propellants such as compressed carbon dioxide have previously been ruled out because the pressure would decrease as doses of the drug were emitted. This would lead to an inconsistent dose being delivered to the patient.

Continued use of HFCs as MDI propellants is undesirable since HFCs also have an undesirable environmental impact (albeit less than the impact of CFCs).

Accordingly, there is a desire to reduce the environmental impact of MDI use, especially as MDI use is predicted to increase.

SUMMARY OF THE INVENTION

In a first aspect, the present invention provides a canister for a metered dose inhaler (MDI), said canister comprising:
a high pressure chamber for containing a liquefied or compressed gas propellant;
a low pressure chamber for containing an inhalable drug and vaporised propellant, the low pressure chamber having an opening for receiving a metering valve; and
a pressure regulating valve interposed between the high pressure chamber and low pressure chamber, the pressure regulating valve adapted to provide a flow path from the high pressure chamber to the low pressure chamber when the pressure in the low pressure chamber drops below a predetermined pressure.

By providing a canister which is divided into a high pressure chamber and a low pressure chamber by a pressure regulating valve, it is no longer necessary to use a propellant (such as an HFC) which maintains a dynamic equilibrium between a liquid and vapour phase. It is possible to use a propellant such as carbon dioxide, nitrogen or nitrous oxide which has a reduced environmental impact. The two chambers and pressure regulating valve ensure that the pressure in the low pressure chamber remains constant throughout the life of the canister so that a consistent dose of drug is maintained.

Optional features of the invention will now be set out. These are applicable singly or in any combination with any aspect of the invention.

In some embodiments, the high pressure chamber and/or the low pressure chamber each comprises a respective connection element for connection to the pressure regulating valve which is interposed between the two chambers. This allows the low pressure chamber containing the non-medicinal product to be manufactured separately from the high pressure chamber and subsequently fitted with the high pressure chamber.

The connection element may be a screw-, snap-, push- or interference fit connection.

In other embodiments, the high and/or low pressure chamber may be integral with the valve body of the pressure regulating valve. In some embodiments, the pressure regulating valve is provided at a lower end of the high pressure chamber. In this case, the high pressure chamber connection element may be provided at a lower end of the high pressure chamber.

In some embodiments, the opening in the low pressure chamber for receiving the metering valve is provided at a lower end of the low pressure chamber. The opening (and the metering valve) provide a path from the low pressure chamber to atmospheric pressure. In some embodiments, the pressure regulating valve is provided at an upper end of the low pressure chamber. In this case, the low pressure chamber connection element may be provided at the upper end of the low pressure chamber.

In some embodiments, the pressure regulating valve is interposed between (and optionally integral with) the lower end of the high pressure chamber and the upper end of the low pressure chamber. This provides a canister having an elongated profile similar to the profile of known canisters so that the inventive canister can be used in a known MDI actuator body. In particular, the low pressure chamber profile may be a truncated version of the profile of a known canister.

In some embodiments, the pressure regulating valve is a mechanical valve i.e. it is operative in response to a change in force on its components as a result of a drop in pressure in the low pressure chamber rather than in response to any electrical signal.

In some embodiments, the pressure regulating valve is a demand valve such as that used in SCUBA dive apparatus. Such a valve can be sourced from Beswick Engineering (USA).

In some embodiments, the pressure regulating valve comprises a resilient element e.g. a coiled spring which biases the pressure regulating valve towards an open position in which there is a flow path from the high pressure chamber to the low pressure chamber. The pressure regulating valve is biased towards a closed position (i.e. with resilient element compressed) by the pressure in the low pressure chamber. The spring constant of the resilient element can be selected to determine the pressure needed in the low pressure chamber to keep the pressure regulating valve in the closed position. Once the pressure in the low pressure chamber drops below this predetermined pressure (as a result of emitting a dose of the inhalable drug from the canister), the resilient element forces the pressure regulating valve to open so that liquefied or compressed gas propellant from the high pressure chamber flows into the head space within the low pressure chamber until the pressure in the low pressure chamber matches the predetermined pressure and the pressure regulating valve is forced to close again.

In some embodiments, the pressure regulating valve comprises a tubular valve stem which is moveable within a valve body defined by a high pressure end wall and a low pressure end wall. Each of the end walls has at least one opening for communication with the respective high pressure/low pressure chamber. The high pressure end wall of the valve body may define the lower end of the high pressure chamber. The low pressure end wall of the valve body may define the upper end of the low pressure chamber.

A gas permeable (liquid-impermeable) member e.g. a porous frit may be provided in the pressure regulating valve or in the low pressure chamber for at least partially blocking the opening in the low pressure end wall of the pressure regulating valve body. This helps to prevent any leakage of the drug from the low pressure chamber.

The tubular valve stem has a high pressure end and a low pressure end. In the closed position, the high pressure end is closed against a valve seat defined by the high pressure end wall by the pressure in the low pressure chamber such that flow from the high pressure chamber through the tubular valve stem is prevented. In the open position, the resilient element biases the high pressure end away from the valve seat/high pressure end wall so that liquefied or compressed gas propellant can flow from the high pressure chamber through the tubular valve stem and into the low pressure chamber through the low pressure end wall of the valve body.

The low pressure end of the tubular valve stem may be provided with a stem flange e.g. an annular stem flange, the stem flange providing a surface upon which the pressure in the low pressure chamber can act against the bias of the resilient element to force the pressure regulating valve into the closed position (with the high pressure end of the tubular valve stem held against the valve seat defined by the high pressure end wall of the valve body). In the open position, the stem flange is forced towards and may abut the low pressure end wall under the force of the resilient element.

The resilient element may be affixed between the stem flange and a valve body flange (e.g. annular flange) depending from a wall of the valve body proximal the high pressure end wall. The resilient element will be compressed between the two flanges in the closed position. The resilient element (e.g. the coiled spring) may surround the tubular valve stem.

The side wall of the valve body may comprise at least one vent (to atmosphere) between the valve body flange and the low pressure end wall to accommodate the changes in the volume defined between the hollow valve stem flange and the valve body flange. The at least one vent is positioned so that it is always on the high pressure side of the valve stem flange.

In a second aspect, the present invention provides a canister for a metered dose inhaler (MDI), said canister comprising:

- a high pressure chamber containing a liquefied or compressed gas propellant;
- a low pressure chamber containing an inhalable drug and vaporised propellant, the low pressure chamber having an opening for receiving a metering valve; and
- a pressure regulating valve interposed between the high pressure chamber and low pressure chamber, the pressure regulating valve adapted to provide a flow path from the high pressure chamber to the low pressure chamber when the pressure in the low pressure chamber drops below a predetermined pressure.

Features of the second aspect may be the same as described for the first aspect.

In preferred embodiments, the liquid propellant is carbon dioxide and the high pressure chamber contains liquefied carbon dioxide. The pressure within the high pressure chamber may be around 6000 kPa or 7000 kPa at 20° C., or even higher such as around 15,000 kPa. The high pressure chamber will typically have a volume of around 10-100 ml.

In this case, the high pressure chamber may be a high pressure carbon dioxide canister such as those supplied by Leland Gases (USA). For example, it may be a 16 g carbon dioxide high pressure cylinder having a volume of 22-23 ml.

Carbon dioxide is especially preferred not only because of its reduced environmental impact compared to HFAs but also because it is readily available (e.g. as a by-product from brewing processes), it is a respiratory stimulant and it is compatible with aqueous alcohol solutions (which may be used to formulate the inhalable drug).

The propellant could also comprise compressed gases such as compressed air, nitrogen, nitrous oxide, oxygen, helium, argon or xenon.

In some embodiments, the low pressure chamber contains a solution, suspension or emulsion of the inhalable drug in an excipient. The excipient may be water and/or ethanol. The low pressure chamber may contain an aqueous solution of the inhalable drug.

The inhalable drug may comprise a bronchodilator such as a beta-agonist (e.g. salbutamol, terbutaline, fenoterol), a long-acting beta-agonist (e.g. salmeterol, formoterol) or an anti-cholinergic (such as ipratropium bromide, tiotropium bromide). The inhalable drug may comprise an anti-inflammatory drug such as a steroid (e.g. beclomethasone, budesonide, ciclesonide, fluticasone, triamcinolone) or a cromoglycate drug (e.g. sodium cromoglycate, nedocromil sodium). The inhalable drug my comprise a vaccine, insulin, antibiotics, anti-fungals, anti-bacterials, anaesthetics, pulmonary anti-hypertensives, anti-inflammatories, pulmonary surfactants or pain medications.

The headspace above the suspension/solution/emulsion of the inhalable drug in the low pressure chamber will be filled with vaporised propellant (e.g. carbon dioxide). The pressure within the low pressure chamber will be above atmospheric pressure. It may be around 300 kPa. It may be at a maximum pressure of around 1000 kPa. The pressure within the low pressure chamber can be selected (in combination with the solvent used to form the solution/suspension/emulsion) to provide the desired particle size of the aerosolized drug.

In a third aspect, the present invention comprises a metered dose inhaler, said metered dose inhaler comprising:
- a canister according to the first or second aspect;
- a metering valve fitted to the opening of the low pressure chamber; and
- an actuator body for housing the canister.

The actuator body may be of the known type i.e. with a substantially upright portion for housing the canister with a laterally-extending mouth piece portion. The base of the upright portion may be provided with a nozzle block having a sump for receiving the valve stem of the metering valve.

The metering valve may be of the known type e.g. such as that manufactured by Bespak.

In other embodiments the canister may have a metering valve according to the fourth aspect described below.

In a fourth aspect, the present invention comprises a metering valve for dispensing a metered dose of product e.g. from a canister containing the product and a propellant, the valve including:
- a metering valve body comprising a propellant metering chamber with a propellant inlet and a product metering chamber with a product inlet; and
- a metering valve stem with a dispensing nozzle, a propellant inlet plug and a product inlet plug, wherein the metering valve stem is movable within the metering valve body to a dispensing position in which:
- the propellant inlet is sealed by the propellant inlet plug and the product inlet is sealed by the product inlet plug; and
- the propellant metering chamber and product metering chamber are in fluid communication with atmosphere via the dispensing nozzle of the metering valve stem such that a metered dose of product and propellant can be dispensed from the metering valve body.

By providing a metering valve having a metering valve body with a separate propellant metering chamber and product metering chamber which are fluid communication with atmosphere via the dispensing nozzle, it is possible to provide a consistent ratio of product (e.g. inhalable drug) and propellant exiting the metering valve body (and thus the canister) such that the control of the particle size of the aerosolised product is optimised for inhalation.

In some embodiments, the metering valve stem is movable within the metering valve body between the dispensing position and at least one filling position in which:
- at least one, and preferably both of the propellant and product inlets are at least partially open such that, in use, propellant can enter the propellant metering chamber (e.g. from within the canister) via the propellant inlet and/or product can enter the product metering chamber (e.g. from within the canister) via the product inlet;
- fluid communication is prevented between the propellant metering chamber and the product metering chamber; and
- fluid communication is prevented between the metering valve body and atmosphere.

In the filling position(s), the propellant and product metering chambers fill with the propellant and product respectively in preparation for dispensing to atmosphere from both chambers in the dispensing position via the dispensing nozzle.

In some embodiments, the metering valve stem is biased towards the at least one filling position by a resilient member such as a coiled spring. The resilient member may be provided in the product metering chamber or the propellant metering chamber. It may surround the metering valve stem in the product/propellant metering chamber.

In some embodiments, the propellant metering chamber and product metering chamber are in fluid communication with one another (and atmosphere via the dispensing nozzle) in the dispensing position. For example, the propellant metering chamber may be in fluid communication with the dispensing nozzle via the product metering chamber. In this way, the propellant and product can be dispensed simultaneously.

In some embodiments the propellant metering chamber may be tubular e.g. cylindrical. The propellant metering chamber may be sized to hold a predetermined quantity of propellant suitable to deliver a single dose of product. The propellant metering chamber may have a volume of between 1000 and 5000 microlitres.

The propellant inlet may be provided at a first axial end of the propellant metering chamber/first axial end of the metering valve body. The inlet may having a tapered e.g. conical surface such that a maximum diameter of the inlet is provided where the propellant inlet opens into the propellant chamber.

The propellant chamber may further comprise a propellant metering valve stem hole for receiving the metering valve stem. This may be provided at a second axial end of the propellant metering chamber. The metering valve stem hole is dimensioned to form a seal around the metering valve stem to prevent leakage of propellant from the propellant metering chamber. The metering valve stem hole may comprise a gasket for assisting sealing around the metering valve stem.

The propellant inlet and propellant metering valve stem hole may be axially co-aligned.

In some embodiments the product metering chamber may be tubular, e.g. cylindrical. The product metering chamber may be sized to hold a predetermined quantity of product. The product metering chamber may have a volume of between 10 and 50 microlitres.

Preferably the relative volume ratio of the product metering chamber to the propellant metering chamber is about 1:100.

The product inlet may be provided at a first axial end of the product metering chamber. The inlet may having a tapered e.g. conical surface such that a maximum diameter of the inlet is provided where the product inlet opens into the product chamber. The product inlet will have a larger (minimum) diameter than the metering valve stem hole (and the metering valve stem) as the metering valve stem will be retained within the product inlet in both the filling and the dispensing position. In the filling position, product will enter the product metering chamber through the product inlet around the metering valve stem.

In embodiments with an axially-arranged product inlet, the metering valve body further comprises at least one side channel (e.g. two diametrically opposed side channels) for providing fluid communication between the canister and the product inlet such that, in use, product can enter the product metering chamber from within the canister via the side channel(s) and the product inlet.

The side channel(s) may open into an intermediate chamber interposed between the propellant metering chamber and product metering chamber e.g. interposed between the second axial end of the propellant metering chamber and the first axial end of the product metering chamber.

The product metering chamber may further comprise a dispensing nozzle hole for receiving the dispensing nozzle of the metering valve stem. This may be provided at a second axial end of the product metering chamber/second axial end of the metering valve body. The dispensing nozzle hole is dimensioned to form a seal around the dispensing nozzle to prevent leakage of product from the product metering chamber.

The axial product inlet and dispensing nozzle hole may be axially co-aligned.

Indeed, all of the propellant inlet, propellant metering valve stem hole, axial product inlet and dispensing nozzle hole may be axially co-aligned The metering valve stem extends within the propellant metering chamber and product metering chamber from the propellant inlet plug at its first axial end (within the propellant metering chamber) to the dispensing nozzle at its second axial end (within the product metering chamber). The product inlet plug is interposed between the propellant inlet plug and the dispensing nozzle.

The metering valve stem is preferably substantially cylindrical.

The propellant inlet plug is dimensioned such that it is able to block/seal the propellant inlet in the dispensing position. Where the propellant inlet has a tapered/conical surface, the propellant inlet plug has a correspondingly shaped surface to form a tight fit within the propellant inlet. The propellant inlet plug may be formed of a rubbery, pliable material or may have a rubbery, pliable coating to help form a seal at the propellant inlet in the dispensing position.

In the filling position, the propellant inlet plug is spaced from the propellant inlet such that the propellant inlet is open to allow fluid communication between the canister and the propellant metering chamber.

The metering valve stem may further comprise a propellant chamber flange (e.g. annular flange) or protrusion extending within the propellant metering chamber. The propellant chamber flange/protrusion acts to limit axial movement of the metering valve stem by abutment against the second axial end of the propellant metering chamber in the filling position. In the filling position, it also helps to seal the metering valve stem hole at the second axial end of the propellant metering chamber thus helping to prevent fluid communication between the propellant metering chamber and the intermediate chamber/product metering chamber. The propellant chamber flange/protrusion may also provide a seat for the resilient member. The resilient member may be retained within the propellant metering chamber between the propellant chamber flange and the first axial end wall of the propellant chamber.

The metering valve stem may further include a propellant channel (comprising a hollow portion of the metering valve stem) which fluidly connects the propellant metering chamber to the product metering chamber when the metering valve stem is in the dispensing position. The propellant channel may have an entrance provided proximal the propellant chamber flange/protrusion with the propellant chamber flange/protrusion interposed between the propellant channel and the propellant inlet plug.

The propellant channel has an exit in the product metering chamber proximal the dispensing nozzle.

In the filling position, the propellant channel entrance is isolated from the propellant metering chamber so that there is no fluid communication between the propellant metering chamber and the product metering chamber. For example, in the filling position, the propellant channel entrance may be located within the intermediate chamber or product metering chamber.

The product inlet plug is dimensioned such that it is able to block/seal the product inlet in the dispensing position. Where the product inlet has a tapered/conical surface, the product inlet plug has a correspondingly shaped surface to form a tight fit within the product inlet.

The product inlet plug may be provided on the metering valve stem interposed between the propellant channel entrance and exit i.e. the propellant channel may pass through the product inlet plug.

The metering valve stem may further comprise a product chamber flange (e.g. annular flange) or protrusion extending within the product metering chamber. The product chamber flange/protrusion acts to limit axial movement of the metering valve stem by abutment against the second axial end of the product metering chamber in the filling position. In the filling position, it also helps to seal the dispensing nozzle hole at the second axial end of the product metering chamber thus helping to prevent fluid communication between the product chamber and the dispensing nozzle/atmosphere. The product chamber flange/protrusion may also provide a seat for the resilient member. The resilient member may be retained within the product metering chamber between the product chamber flange and the first axial end wall of the product chamber.

The dispensing nozzle is a hollow tube having a side port and an axial port. In the filling position, both the side port and axial port are located externally of the product metering chamber such that there is no fluid communication between the product metering chamber and the dispense nozzle.

In the dispensing position, the side port is located within the product chamber such that there is fluid communication between the product metering chamber and the axial port of the dispense nozzle (which vents to atmosphere).

To summarise, in the filling position, the propellant inlet is unobstructed by the propellant inlet plug and the metering valve stem hole is blocked/sealed by the metering valve stem and by abutment of the propellant chamber flange/protrusion against the second axial wall of the propellant metering chamber. The entrance to the propellant channel is outside the propellant metering chamber (within the intermediate chamber) such that there is no flow of propellant through the channel. In use, the propellant chamber fills with propellant e.g. vaporised propellant e.g. vaporised carbon dioxide from within the canister.

The product inlet is unobstructed by the product inlet plug and the dispensing nozzle hole is blocked/sealed by the dispense nozzle and by abutment of the product chamber flange/protrusion against the second axial wall of the product metering chamber. The side port of the dispensing nozzle is outside the product metering chamber (outside the metering valve body) such that there is no flow of product through the dispensing nozzle. In use, the product chamber fills with product e.g. product solution from the canister via the side channels, intermediate chamber and product inlet. There will also be flow of product through the propellant channel since the entrance to the propellant channel is located within the intermediate chamber.

In the dispensing position, the metering valve stem moves into the metering valve body and the propellant inlet and product inlet are sealed by the propellant inlet plug and product inlet plug respectively. This movement unseats the propellant/product chamber flanges/protrusions from their respective axial end walls.

The entrance to the propellant channel moves within the propellant metering chamber and the side port of the dispense nozzle moves within the product metering chamber. Propellant flows through the propellant channel into the product metering chamber simultaneously with product (and propellant) moving from the product metering chamber into atmosphere via the dispensing nozzle.

In a fifth aspect the present invention comprises a canister according to the first or second aspect having a metering valve according to the fourth aspect.

The metering valve is provided in the low pressure chamber with the propellant metering chamber in fluid communication with the headspace containing vaporised propellant (e.g. vaporised carbon dioxide) and the product metering chamber in fluid communication with the product solution.

In a sixth aspect, the present invention comprises a metered dose inhaler, said metered dose inhaler comprising:
a canister according to the fifth aspect; and
an actuator body for housing the canister.

The actuator body may be of the known type i.e. with a substantially upright portion for housing the canister with a laterally-extending mouth piece portion. The base of the upright portion may be provided with a nozzle block having a sump for receiving the valve stem of the metering valve.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

Figure 1:
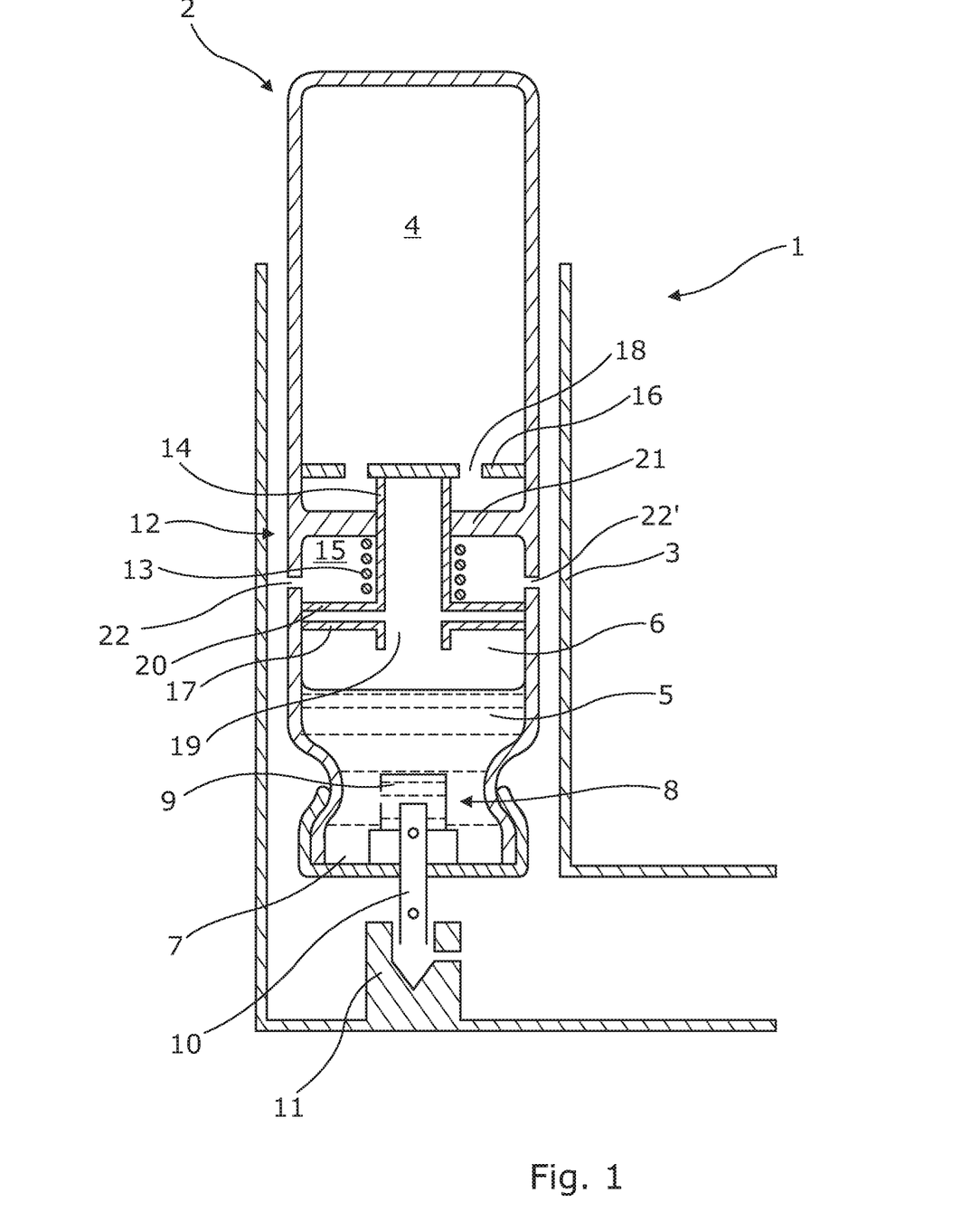
FIG. 1 shows a first embodiment of a metered dose inhaler comprising a canister with the pressure regulating valve in the closed position.
Figure 2:
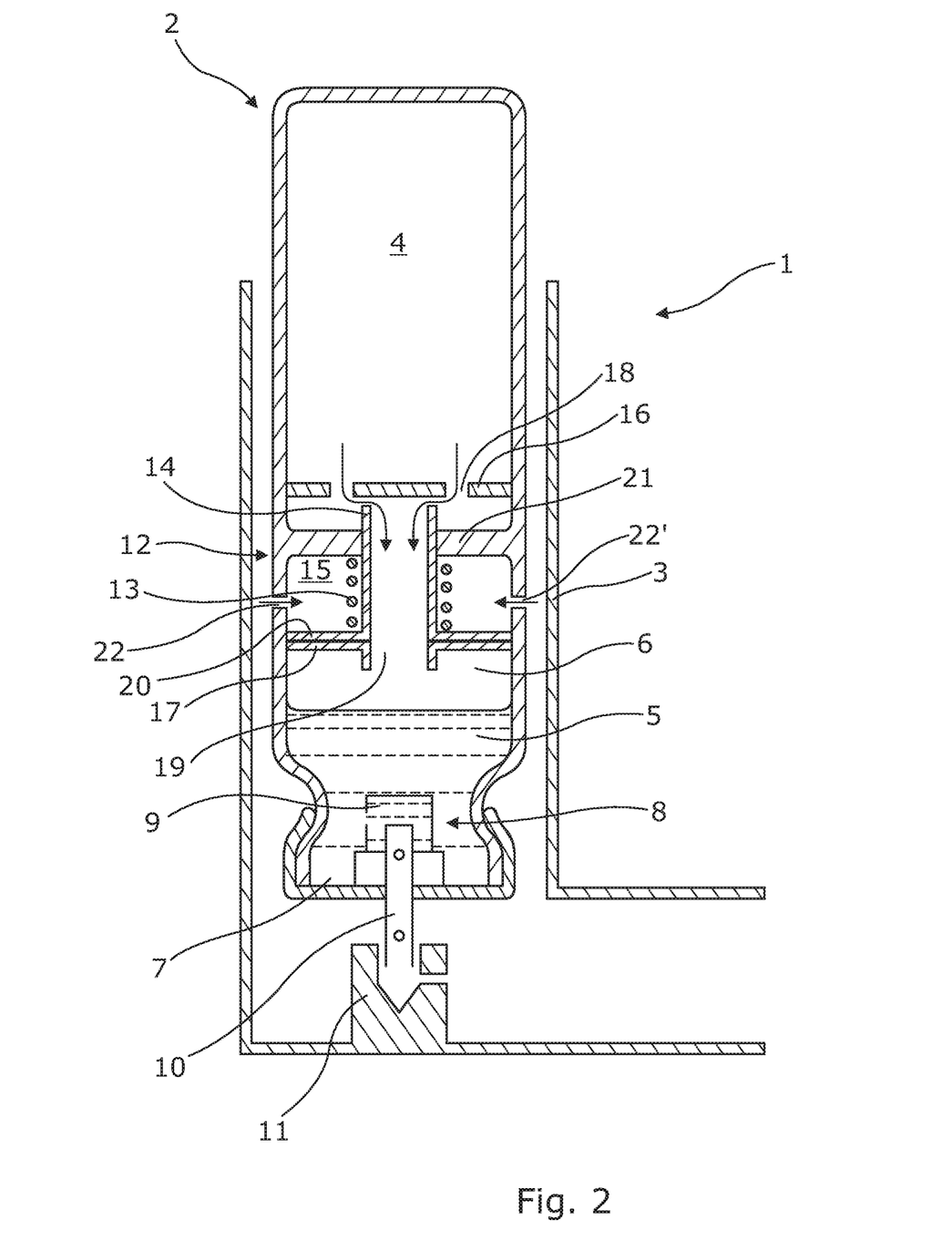
FIG. 2 shows the first embodiment comprising a canister with the pressure regulating valve in the open position.
Figure 6:
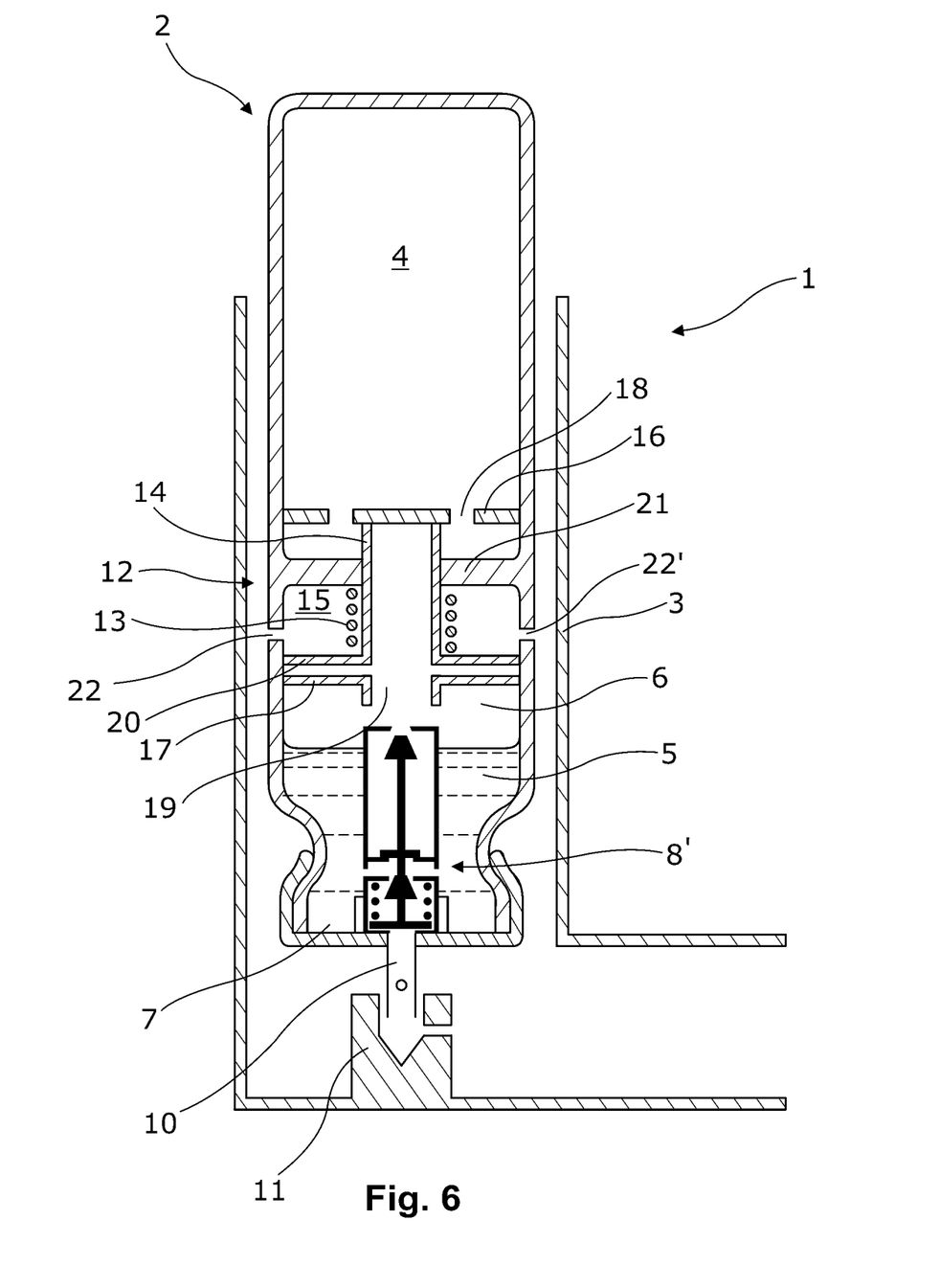
FIG. 6 shows the first embodiment of the metered dose inhaler comprising a canister with the pressure regulating valve in the closed position and the metering valve according to the fourth aspect of the present invention in a filling position.

FIGS. 1, 2, and 6 show a metered dose inhaler (MDI) 1 having a canister 2 housed within an actuator body 3.

The canister 2 comprises a high pressure chamber 4 which is a high pressure carbon dioxide canister containing around 16 g (12 g-22 g) liquefied carbon dioxide. Such a high pressure carbon dioxide canister may be obtained from Leland Gases (USA). The pressure within the high pressure chamber 4 is around 7000 kPa.

The canister further comprises a low pressure chamber 5 containing a concentrated (25 mg/ml) aqueous solution of an inhalable drug (salbutamol sulphate). The headspace 6 within the chamber 5 contains gaseous carbon dioxide. The pressure within the low pressure chamber 5 is above atmospheric pressure and around 300 kPa.

The low pressure chamber 5 has an opening 7 at its lower end for receiving a metering valve 8. The metering valve 8 is of a known type (e.g. manufactured by Bespak) comprising a metering chamber 9 and a valve stem 10, the valve stem 10 being received in a nozzle block 11 at the base of the actuator body 3.

The low pressure chamber 5 can be filled with the aqueous solution of the inhalable drug before crimping of the metering valve 8 or it can be filled through the metering valve 8. Both options are current practice.

The canister further comprises a pressure regulating valve 12 interposed between the high pressure chamber 4 and low pressure chamber 5.

The low pressure chamber 5 is primed with carbon dioxide to fill the head space 6 after connection of the pressure regulating valve 12 and the high pressure chamber 4.

The pressure regulating valve 12 is adapted to provide a flow path from the high pressure chamber 4 to the low pressure chamber 5 when the pressure in the low pressure chamber 5 drops below a predetermined pressure.

By providing a canister which is divided into a high pressure chamber and a low pressure chamber by a pressure regulating valve, it is possible to use a propellant such as carbon dioxide which has a reduced environmental impact compared to the currently used HFCs. The two chambers 4, 5 and pressure regulating valve 12 ensure that the pressure in the low pressure chamber 5 remains constant throughout the life of the canister 2 so that a consistent dose of drug is maintained as discussed below.

The pressure regulating valve 12 is interposed between a lower end of the high pressure chamber 4 and an upper end of the low pressure chamber 5. This provides a canister 2 having an elongated profile similar to the profile of known canisters so that the inventive canister can be used in a known MDI actuator body 3.

Each of the lower end of the high pressure chamber 4 and the upper end of the low pressure chamber 5 has a screw-, snap- or push-fit connection element for connection to the pressure regulating valve 12.

The pressure regulating valve 12 is a mechanical valve i.e. it is operative in response to a change in force on its components as a result of a drop in pressure in the low pressure chamber rather than in response to any electrical signal.

The pressure regulating valve similar to a demand valve such as that used in SCUBA dive apparatus.

The pressure regulating valve 12 comprises a coiled spring 13 which biases the valve towards an open position (shown in FIG. 2) in which there is a flow path from the high pressure chamber 4 to the low pressure chamber 4. The pressure regulating valve 12 is biased towards a closed position (i.e. against the bias of the coiled spring 13) by the pressure in the low pressure chamber 5 (shown in FIG. 1). The spring constant of the coiled spring 13 can be selected to determine the pressure needed in the low pressure chamber 5 to keep the pressure regulating valve 12 in the closed position.

Once the pressure in the low pressure chamber 5 drops below this predetermined pressure (as a result of emitting a dose of the inhalable drug from the canister 2), the coiled spring 13 forces the pressure regulating valve 12 to open so that liquefied carbon dioxide from the high pressure chamber 4 flows into and vaporises within the head space 6 within the low pressure chamber 5 until the pressure in the low pressure chamber 5 matches the predetermined pressure once more and the pressure regulating valve 12 is forced to close.

The pressure regulating valve 12 comprises a tubular valve stem 14 which is moveable within a valve body 15 defined by a high pressure end wall 16 and a low pressure end wall 17. Each of the end walls 16, 17 has at least one opening 18, 19 for communication with the respective high pressure/low pressure chamber 4, 5.

The tubular valve stem 14 has a high pressure end and a low pressure end. In the closed position shown in FIG. 1, the high pressure end is sealed against a valve seat defined by the high pressure end wall 16 by the pressure in the low pressure chamber 5 such that flow from the high pressure chamber 4 through the tubular valve stem 14 is prevented. In the open position shown in FIG. 2, the drop in pressure in the low pressure chamber 5 arising from actuation of the canister, allows the coiled spring 13 to pull the high pressure end away from the valve seat/high pressure end wall 16 so that liquefied carbon dioxide can flow from the high pressure chamber 4 through the tubular valve stem 14 and into the low pressure chamber 5 through the low pressure end wall 17 of the valve body 15.

This increases the pressure within the low pressure chamber 5 until the pressure regulating valve 12 is forced back to the closed position against the bias of the coiled spring 13 once the predetermined pressure is reached.

The low pressure end of the tubular valve stem 14 is provided with an annular stem flange 20, the stem flange 20 providing a surface upon which the pressure in the low pressure chamber 5 can act against the bias of the coiled spring 13 to force the pressure regulating valve 12 into the closed position shown in FIG. 1 (with the high pressure end of the tubular valve stem 14 held against the valve seat defined by the high pressure end wall 16 of the valve body 15). In the open position, the annular stem flange 20 is forced towards and abuts the low pressure end wall 17 under the force of the coiled spring 13 as shown in FIG. 2.

The coiled spring 13 is affixed between the stem flange 20 and an annular valve body flange 21 depending from a side wall of the valve body 15 proximal the high pressure end wall 16. The coiled spring 13 is compressed between the two flanges 20, 21 in the closed position shown in FIG. 1. The coiled spring 13 surrounds the tubular valve stem 14.

The side walls of the valve body 15 comprise vents 22, 22' (to atmosphere) between the valve body flange 21 and the low pressure end wall 17 to accommodate the changes in the volume defined between the hollow valve stem flange 20 and the valve body flange 21 during actuation of the valve. The vents 22, 22' are positioned so that they are always on the high pressure side of the valve stem flange 20. As the tubular valve stem 14 moves to the open position, air will be drawn through the vents 22, 22'. As the tubular valve stem 14 moves to the closed position, air will be pushed out through the vents 22, 22'.

As discussed above, the arrangement of the high pressure chamber 4, low pressure chamber 5 and the pressure regulating valve 12, ensures a constant pressure is maintained within the low pressure chamber 5 by flow and vaporisation of liquid carbon dioxide from the high pressure chamber 4 when the pressure in the low pressure chamber 5 drops below a predetermined pressure. This constant pressure in the low pressure chamber ensures a consistent dose of inhalable drug is delivered each time.

Figure 3:
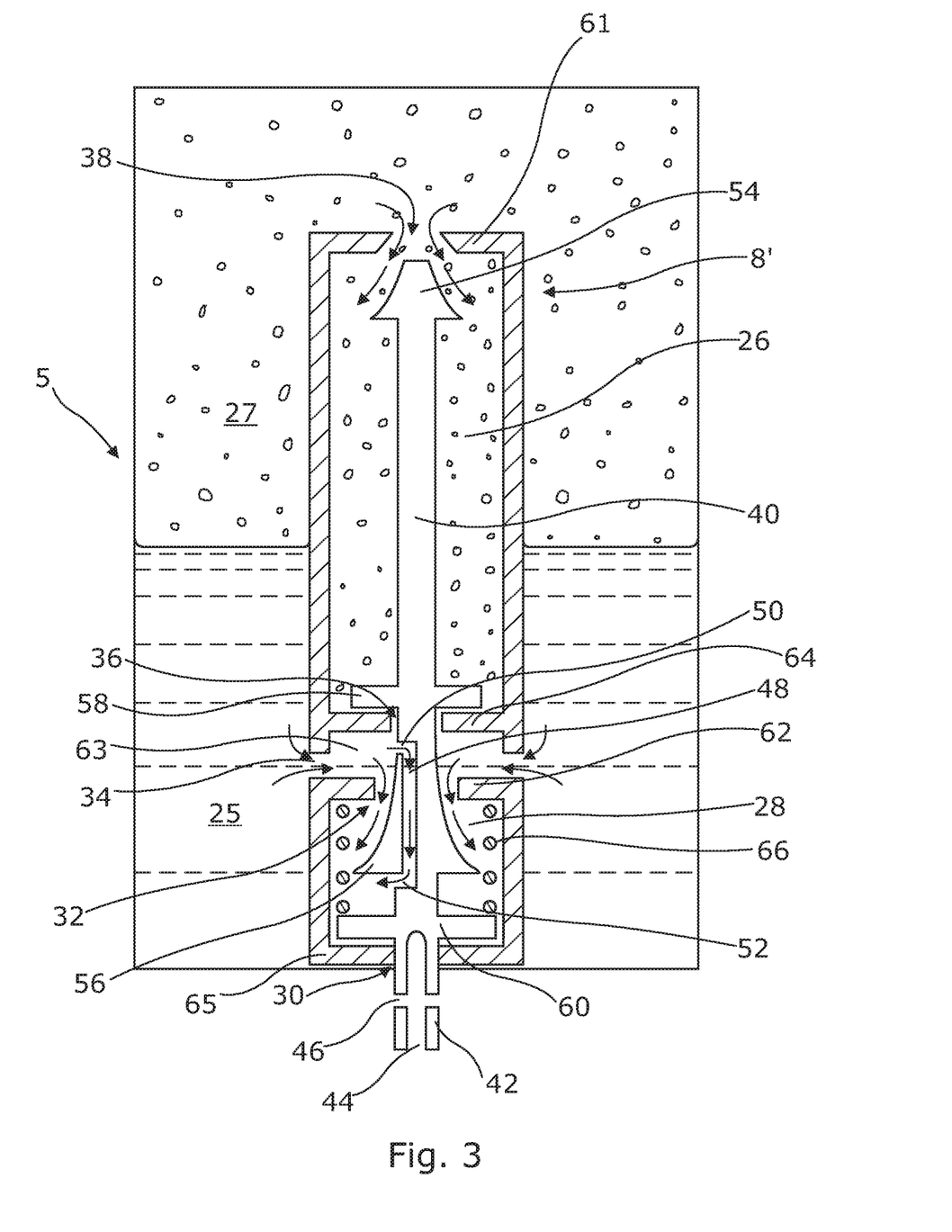
FIG. 3 shows a metering valve according to the fourth aspect of the present invention in a filling position.

FIG. 3 is a cross-section through an embodiment of a metering valve 8' according to the fourth aspect of the present invention.

The metering valve 8' is located in an opening 7 of a low pressure chamber 5 of a canister (as also shown in FIG. 6) according to the first embodiment. The low pressure chamber 5 contains an aqueous suspension of salbutamol 25 and gaseous carbon dioxide 27.

The metering valve 8' comprises a metering valve body comprising a propellant metering chamber 26 with a propellant inlet 38 and a product metering chamber 28 with a product inlet 32.

The propellant metering chamber 26 is defined by tubular walls such that the propellant metering chamber is a tubular/cylindrical chamber. The propellant metering chamber has a volume of around 3000 microlitres.

The propellant inlet 38 is provided at a first axial end 61 of the propellant metering chamber 26 which is also the first axial end of the metering valve body. The propellant inlet 38 has a tapered, conical surface such that a maximum diameter of the propellant inlet 38 is provided where the propellant inlet 38 opens into the propellant chamber 26.

The product metering chamber 28 is defined by tubular walls such that the product metering chamber 28 is a tubular/cylindrical chamber. The product metering chamber 28 has a volume of around 30 microlitres i.e. relative volume ratio of the product metering chamber 28 to the propellant metering chamber 26 is about 1:100.

The product inlet 32 is provided at a first axial end 62 of the product metering chamber 26. The product inlet 32 has a tapered, conical surface such that a maximum diameter of the product inlet 32 is provided where the product inlet 32 opens into the product chamber 26.

The metering valve 8' also comprises a metering valve stem 40 which extends axially within the valve body from a propellant inlet plug 54 at its first axial end located within the propellant chamber 26 to a dispensing nozzle 42 at its second axial end located within the partially within the product chamber 28. A product inlet plug 56 is also provided on the metering valve stem interposed between the propellant inlet plug 54 and the dispensing nozzle 42.

The metering valve stem 40 is movable within the valve body to a dispensing position (shown in FIG. 4) in which product (salbutamol) and propellant (carbon dioxide) are dispensed from the metering valve. In the dispensing position, the propellant inlet 38 is sealed by the propellant inlet plug 54 and the product inlet 32 is sealed by the product inlet plug 56.

Figure 4:
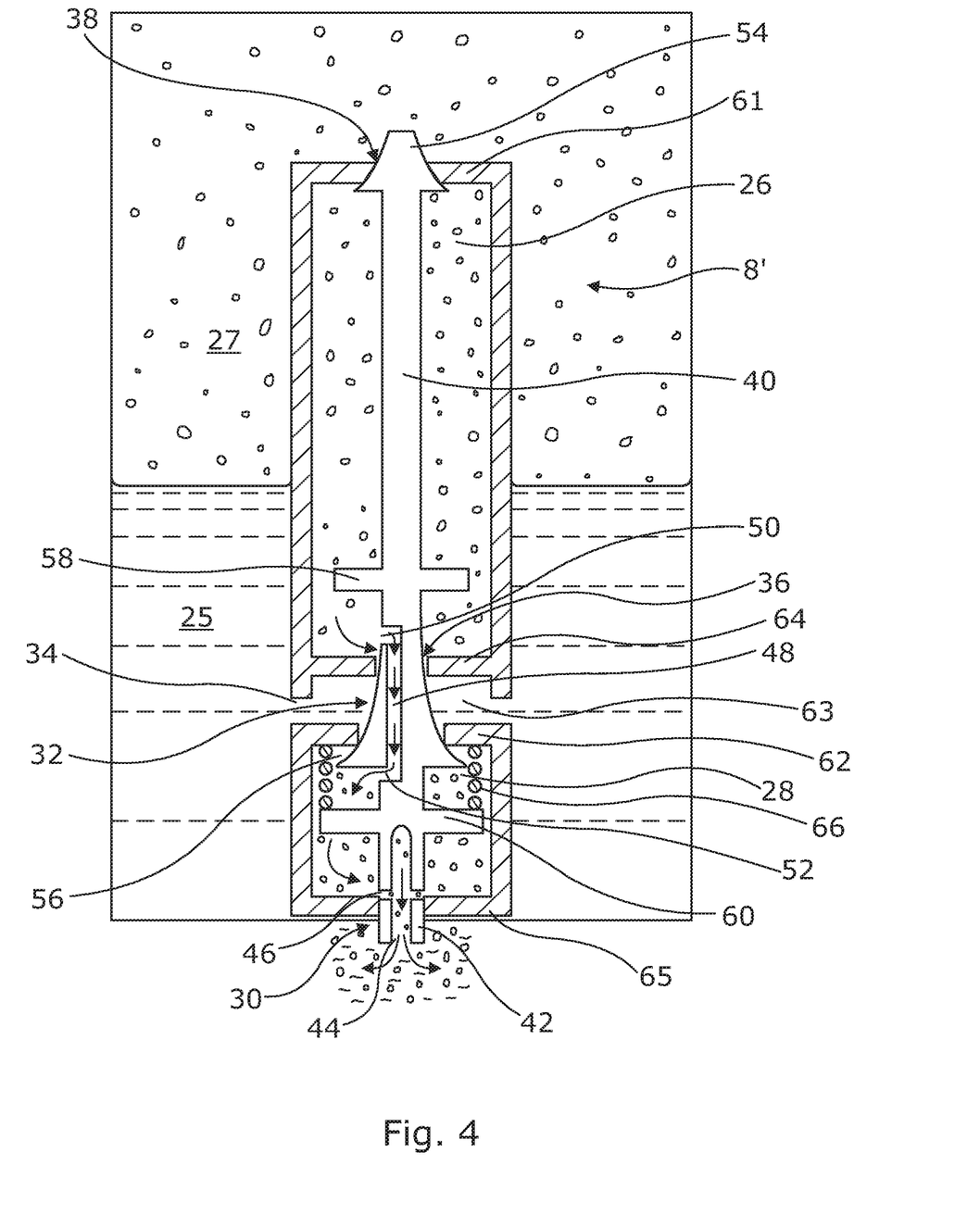
FIG. 4 shows the metering valve of FIG. 3 in a dispensing position.

The propellant inlet plug 54 is dimensioned such that it is able to block/seal the propellant inlet in a dispensing position. The propellant inlet plug 54 has a tapered, conical surface to form a tight fit within the propellant inlet 38.

The product inlet plug 56 is dimensioned such that it is able to block/seal the product inlet 32 in the dispensing position. The product inlet plug 56 has a tapered, conical surface to form a tight fit within the product inlet 32.

Furthermore, in the dispensing position, the propellant metering chamber 26 and product metering chamber 28 are in fluid communication with atmosphere via the dispensing nozzle 42 of the metering valve stem 40 such that a metered dose of product (salbutamol) and propellant (carbon dioxide) can be dispensed from the metering valve body. The propellant metering chamber 26 and product metering chamber 28 are in fluid communication with one another in the dispensing position i.e. the propellant metering chamber 26 is in fluid communication with the dispensing nozzle 42 via the product metering chamber 28.

The metering valve stem 40 is movable within the metering valve body between the dispensing position (shown in FIG. 4) and a filling position (shown in FIG. 3) in which the propellant and product metering chambers 26, 28 fill with the propellant and product respectively in preparation for dispensing to atmosphere from both chambers in the dispensing position via the dispensing nozzle In the filling position, the propellant inlet 38 and product inlet 32 are at least partially open such that propellant (gaseous carbon dioxide) can enter the propellant metering chamber 26 from within the head space 27 of the low pressure chamber 5 of the canister via the propellant inlet 38 and product (salbutamol) can enter the product metering chamber 28 from within the low pressure chamber 5 of the canister via the product inlet 32.

In the filling position, the propellant inlet plug 54 is spaced from the propellant inlet 38 such that the propellant inlet 38 is open to allow fluid communication between the low pressure chamber 5 of the canister and the propellant metering chamber 26.

To allow access to the product inlet 32, an intermediate chamber 63 is provided interposed between the propellant metering chamber 26 and product metering chamber 28.

The intermediate chamber 63 has two diametrically opposed side channels 34 for providing fluid communication between the low pressure chamber 5 of the canister and the product inlet 32 such that, in use, the salbutamol suspension 25 can enter the product metering chamber 28 from the low pressure chamber 5 via the side channels 34 and the product inlet 32.

Furthermore, in the filling position, fluid communication is prevented between the propellant metering chamber 26 and the product metering chamber 28 and fluid communication is prevented between the metering valve body and atmosphere.

The propellant chamber 26 further comprises a propellant metering valve stem hole 36 for receiving the metering valve stem 40. This is provided at a second axial end 64 of the propellant metering chamber 26. The metering valve stem hole 36 is dimensioned to form a seal around the metering valve stem 40 to prevent leakage of propellant from the propellant metering chamber 26.

The propellant inlet 38 and propellant metering valve stem hole 36 are axially co-aligned.

The product metering chamber 28 further comprises a dispensing nozzle hole 30 for receiving the dispensing nozzle 42 of the metering valve stem 40. This is provided at a second axial end 65 of the product metering chamber 28 which is also the second axial end of the metering valve body. The dispensing nozzle hole 30 is dimensioned to form a seal around the dispensing nozzle to prevent leakage of the salbutamol solution from the product metering chamber 28.

The product inlet 32 and dispensing nozzle hole 30 are axially co-aligned with one another and also axially aligned with the propellant inlet 38 and propellant metering valve stem hole 36.

The product inlet 32 has a larger (minimum) diameter than the metering valve stem hole 36 (and the metering valve stem 40) as the metering valve stem 40 is retained within the product inlet 32 in both the filling and the dispensing positions. In the filling position, salbutamol suspension 25 will enter the product metering chamber 28 through the product inlet 32 around the metering valve stem 40.

The metering valve stem 40 further comprises a propellant chamber annular flange 58 extending within the propellant metering chamber 26. The propellant chamber annular flange 58 acts to limit axial movement of the metering valve stem 40 by abutment against the second axial end 64 of the propellant metering chamber 26 in the filling position. In the filling position, it also helps to seal the metering valve stem hole 36 at the second axial end 64 of the propellant metering chamber 26 thus helping to prevent fluid communication between the propellant metering chamber 26 and the intermediate chamber 63/product metering chamber 28.

The metering valve stem 40 further includes a propellant channel 48 (comprising a hollow portion of the metering valve stem) which fluidly connects the propellant metering chamber 26 to the product metering chamber 28 when the metering valve stem 40 is in the dispensing position. The propellant channel 48 has an entrance 50 provided proximal the propellant chamber annular flange 58 with the propellant chamber annular flange 58 interposed between the propellant channel 48 and the propellant inlet plug 54.

The propellant channel 48 has an exit 52 in the product metering chamber 28 proximal the dispensing nozzle 42.

In the filling position, the propellant channel entrance 50 is isolated from the propellant metering chamber 26 so that there is no fluid communication between the propellant metering chamber 26 and the product metering chamber 28. In the filling position, the propellant channel entrance 50 is located within the intermediate chamber 63.

The product inlet plug 56 is provided on the metering valve stem 40 interposed between the propellant channel entrance 50 and exit 52 i.e. the propellant channel 48 passes through the product inlet plug 56.

The metering valve stem 40 further comprises a product chamber annular flange 60 extending within the product metering chamber. The product chamber annular flange 60 acts to limit axial movement of the metering valve stem 40 by abutment against the second axial end 65 of the product metering chamber 28 in the filling position. In the filling position, it also helps to seal the dispensing nozzle hole 30 at the second axial end 65 of the product metering chamber 28 thus helping to prevent fluid communication between the product chamber 28 and the dispensing nozzle 42/atmosphere.

The metering valve comprises a resilient member 66 which is a coiled spring surrounding the metering valve stem 40 within the product metering chamber 28. The resilient member 66 is retained between the product chamber annular flange and the first axial end wall 62 of the product metering chamber 28.

The dispensing nozzle 42 is a hollow tube having a side port 46 and an axial port 44. In the filling position, both the side port 46 and axial port 44 are located externally of the product metering chamber 28 such that there is no fluid communication between the product metering chamber 48 and the dispense nozzle 42.

In the dispensing position, the side port 46 is located within the product chamber 28 such that there is fluid communication between the product metering chamber 28 and the axial port 44 of the dispense nozzle 42 (which vents to atmosphere).

To summarise, in the filling position (shown in FIG. 3), the propellant inlet 38 is unobstructed by the propellant inlet plug 54 and the metering valve stem hole 36 is blocked/sealed by the metering valve stem 40 and by abutment of the propellant chamber annular flange 58 against the second axial wall 64 of the propellant metering chamber 26. The entrance 50 to the propellant channel 48 is outside the propellant metering chamber 26 (within the intermediate chamber 63) such that there is no flow of propellant through the channel 48. The propellant metering chamber 26 fills with propellant i.e. vaporised carbon dioxide from within the headspace of the low pressure chamber 5 of the canister.

The product inlet 32 is unobstructed by the product inlet plug 56 and the dispensing nozzle hole 30 is blocked/sealed by the dispense nozzle 42 and by abutment of the product chamber annular flange 60 against the second axial wall 65 of the product metering chamber 28. The side port 46 of the dispensing nozzle 42 is outside the product metering chamber 28 (outside the metering valve body) such that there is no flow of product (Salbutamol) through the dispensing nozzle 42. The product chamber 28 fills with salbutamol from the low pressure chamber 5 of the canister via the side channels 34, intermediate chamber 63 and product inlet 32. There is also a flow of Salbutamol through the propellant channel 48 since the entrance 50 to the propellant channel 48 is located within the intermediate chamber 63.

The metering valve is biased towards the filling position by the resilient member 66. To move the metering valve to the dispensing position (shown in FIG. 4), the canister is depressed such that the resilient member 60 is compressed and the metering valve stem 40 moves into the metering valve body. The propellant inlet 38 and product inlet 32 are sealed by the propellant inlet plug 56 and product inlet plug 54 respectively. This movement unseats the propellant/product chamber annular flanges 36, 60 from their respective axial end walls 64, 65.

The entrance 50 to the propellant channel 48 moves within the propellant metering chamber 26 and the side port 46 of the dispense nozzle 42 moves within the product metering chamber 28. Propellant (carbon dioxide) flows through the propellant channel 48 into the product metering chamber 26 simultaneously with Salbutamol (and carbon dioxide) moving from the product metering chamber 28 into atmosphere via the dispensing nozzle 42.

Figure 5:
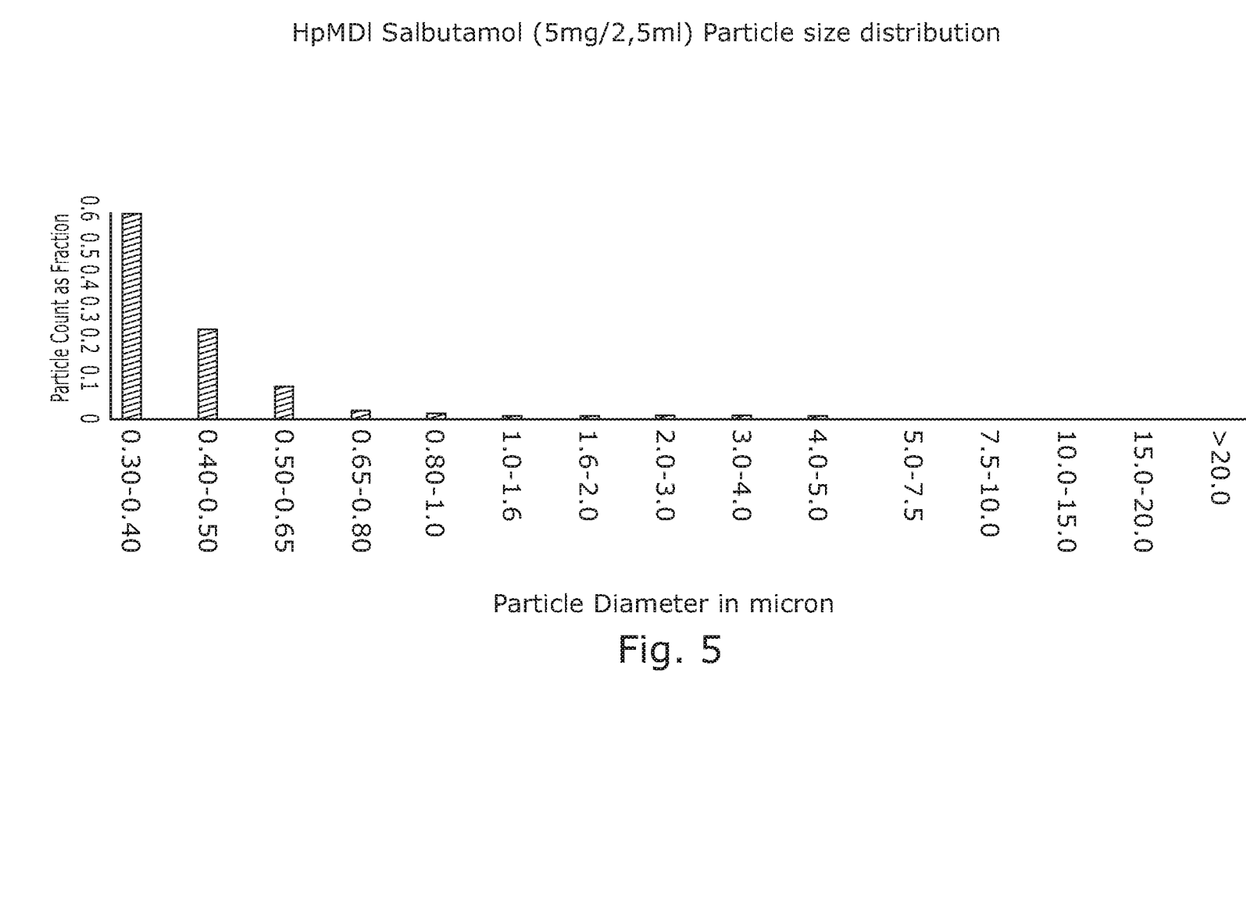
FIG. 5 shows a particle size distribution of 5 mg/2.5 ml of Salbutamol dispensed from a metering valve according to the fourth aspect of the present invention.

FIG. 5 shows a particle size distribution for a 5 mg/2.5 ml dose of salbutamol dispensed from a product metering chamber 28 of 30 microlitres capacity at 5.5 bar using a carbon dioxide propellant. The particle size distribution has been determined by an optical particle counter, Grimm 1.109. The instrument measures particle counts (particle/m$^3$) from 0.3 to 20 micron. As can be seen, over half of the salbutamol particles have a diameter of 0.3 to 0.4 microns and substantially all of the particles are in the respirable range, i.e. have a diameter of <5 micron. Aerosol particles in this range have a high probability of penetrating beyond the upper airways and depositing in the lungs. The metering valve therefore allows carbon dioxide to be used as a propellant to dispense inhalable drugs with a suitable particle size distribution to be effectively administered to a patient.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

The invention claimed is:

1. The canister for a metered dose inhaler (MDI), the canister comprising:
   a high pressure chamber containing a liquefied or compressed propellant, the propellant selected from carbon dioxide, air, nitrogen, oxygen, helium, argon and xenon;
   a low pressure chamber containing an inhalable drug and vaporised propellant, the low pressure chamber having an opening for receiving a metering valve; and
   a pressure regulating valve interposed between a lower end of the high pressure chamber and an upper end of the low pressure chamber, the pressure regulating valve adapted to provide a flow path from the high pressure chamber to the low pressure chamber when a pressure in the low pressure chamber drops below a predetermined pressure.

2. The canister according to claim 1 wherein the opening in the low pressure chamber for receiving the metering valve is provided at a lower end of the low pressure chamber.

3. The canister according to claim 1 wherein the pressure regulating valve is a mechanical valve.

4. The canister according to claim 3 wherein the pressure regulating valve comprises a resilient element which biases the pressure regulating valve towards an open position in which there is the flow path from the high pressure chamber to the low pressure chamber.

5. The canister according to claim 3 wherein the pressure regulating valve comprises a tubular valve stem having a high pressure end and a low pressure end, and which is moveable within a valve body defined by a high pressure end wall and a low pressure end wall.

6. The canister according to claim 5 wherein, in a closed position, the high pressure end is closed against a valve seat defined by the high pressure end wall by the pressure in the low pressure chamber such that flow from the high pressure chamber through the tubular valve stem is prevented.

7. The canister according to claim 5 wherein the low pressure end of the tubular valve stem is provided with a stem flange, the stem flange providing a surface upon which the pressure in the low pressure chamber can act against a bias of a resilient element to force the pressure regulating valve into a closed position.

8. The canister according to claim 1 wherein the metering valve is for dispensing a metered dose of product from the canister containing the product and the propellant, the metering valve including:
   a metering valve body comprising a propellant metering chamber with a propellant inlet and a product metering chamber with a product inlet; and
   a metering valve stem comprising (i) a propellant channel having an entrance and an exit, (ii) a dispensing nozzle formed as a hollow tube having a side port and an axial port, (iii) a propellant inlet plug, and (iv) a product inlet plug,
   wherein the metering valve stem is movable within the metering valve body to a dispensing position in which:
   the propellant inlet is sealed by the propellant inlet plug and the product inlet is sealed by the product inlet plug;
   the propellant channel entrance is located in the propellant metering chamber and the propellant channel exit is located within the product metering chamber such that the propellant metering chamber is in fluid communication with the product metering chamber via the propellant channel, and is in fluid communication with the dispensing nozzle via the product metering chamber; and
   the dispensing nozzle side port is located within the product metering chamber such that the product metering chamber is in fluid communication with atmosphere via the dispensing nozzle such that the metered dose of the product and the propellant can be dispensed from the canister via the product metering chamber,
   wherein the metering valve is provided in the low pressure chamber.

9. A metered dose inhaler, said metered dose inhaler comprising:
   a canister according to claim 1;
   a metering valve fitted to the opening of the low pressure chamber; and
   an actuator body for housing the canister.

10. The canister for a metered dose inhaler (MDI), the canister comprising:

a high pressure chamber containing a liquefied or compressed propellant, the propellant selected from carbon dioxide, air, nitrogen, oxygen, helium, argon and xenon;

a low pressure chamber containing an inhalable drug and vaporised propellant, the low pressure chamber having an opening for receiving a metering valve; and a mechanical pressure regulating valve interposed between a lower end of the high pressure chamber and an upper end of the low pressure chamber, the pressure regulating valve comprising a tubular valve stem having a high pressure end and a low pressure end and which is moveable within a valve body defined by a high pressure end wall and a low pressure end wall so as to provide a flow path from the high pressure chamber to the low pressure chamber when a pressure in the low pressure chamber drops below a predetermined pressure.

* * * * *